United States Patent [19]
Deasy et al.

[11] Patent Number: 5,668,371
[45] Date of Patent: Sep. 16, 1997

[54] METHOD AND APPARATUS FOR PROTON THERAPY

[75] Inventors: Joseph O. Deasy, Louisville, Ky.; Thomas R. Mackie; Paul M. DeLuca, Jr., both of Madison, Wis.

[73] Assignee: Wisconsin Alumni Research Foundation, Madison, Wis.

[21] Appl. No.: 722,727

[22] Filed: Oct. 1, 1996

Related U.S. Application Data

[63] Continuation of Ser. No. 469,413, Jun. 6, 1995, abandoned.

[51] Int. Cl.⁶ .................. G01N 23/225; H01J 37/147; H01J 37/30
[52] U.S. Cl. ........................... 250/306; 250/505.1
[58] Field of Search ................ 250/306, 505.1, 250/307

[56] References Cited

U.S. PATENT DOCUMENTS

| | | | |
|---|---|---|---|
| 4,672,212 | 6/1987 | Brahme | 250/505.1 |
| 4,868,843 | 9/1989 | Nunan | 250/505.1 |
| 5,012,506 | 4/1991 | Span et al. | 250/505.1 |
| 5,019,713 | 5/1991 | Schmidt | 250/505.1 |
| 5,166,531 | 11/1992 | Huntzinger | 250/505.1 |
| 5,317,616 | 5/1994 | Swerdloff et al. | 378/65 |
| 5,440,133 | 8/1995 | Moyers et al. | 250/492.3 |

OTHER PUBLICATIONS

*Radiotherapy and Oncology*, Journal of the European Society for Therapeutic Radiology and Oncology, vol. 15/2, 1989.

*Primary Examiner*—Bruce Anderson
*Attorney, Agent, or Firm*—Quarles & Brady

[57] ABSTRACT

A method of proton tomotherapy provides uniform dose placement within a tumorous area on a slice by slice basis by locating a Bragg peak of the proton beam at the distal edge of the tumor and irradiating the tumor from a number of different angles without sweeping the range of the protons at the given angle. Uniform dose is provided by simultaneous intensity modulation of the beams. Treatment of the tumor in slices eliminates the need for a rotating gantry but allows the patient to be rotated instead. Accurate range placement is provided by a preliminary proton verification tomogram obtainable on the same equipment. A set of standard blocks permits this technique to be used with standard irradiation zones without additional range or intensity adjusting mechanism.

5 Claims, 3 Drawing Sheets

METHOD AND APPARATUS FOR PROTON THERAPY

This is a continuation of application Ser. No. 08/469,413, filed Jun. 6, 1995, abandoned.

This invention was made with United States government support awarded by NIH, Grant #GRANT #CA09206. The United States Government has certain rights in this invention.

FIELD OF THE INVENTION

This invention relates generally to radiation therapy equipment for the treatment of tumors or the like and specifically to a method and apparatus for proton therapy.

BACKGROUND ART

Medical equipment for radiation therapy treats tumorous tissue with high energy radiation. The dose and placement of the dose must be accurately controlled to ensure both that the tumor receives sufficient radiation to be destroyed, and that damage to the surrounding and adjacent non-tumorous tissue is minimized.

Internal source radiation therapy places capsules of radioactive material inside the patient in proximity to the tumorous tissue. Dose and placement are accurately controlled by the physical positioning of the isotope; however, internal source radiation therapy has the disadvantage of any surgically invasive procedure, including discomfort to the patient and risk of infection.

External source radiation therapy uses a radiation source that is external to the patient. The external source produces a collimated beam of radiation directed into the patient to the tumor site. External source radiation therapy avoids some of the problems of internal source radiation therapy, but it undesirably and necessarily irradiates a significant volume of non-tumorous or healthy tissue in the path of the radiation beam to the tumorous tissue.

The adverse effect of irradiating healthy tissue may be reduced while still maintaining a given dose of radiation in the tumorous tissue by projecting the external radiation beam into the patient at a variety of "gantry angles" with the beams converging on the tumor site. In this way, the particular volume elements of healthy tissue along the path of the radiation beam change as the gantry angle changes reducing the total dose to each such element of healthy tissue. The tumor, at the site of convergence of the beams, receives a cumulative, greater dose.

Radiation therapy systems employing high energy x-rays, such as from a linear accelerator, can control the placement of the dose very accurately by changing the intensity of the multiple rays of the treatment beam as a function of beam angle. Accurate computer control of the intensity of the radiation beam, over a range of angles, allows the irradiation of tumors having, for example, a concave cross-section—a dose pattern difficult to obtain with conventional radiotherapy techniques. Such a computer controlled system is described in U.S. Pat. No. 5,317,616 issued May 31, 1994 and assigned to the same assignees as the present invention and hereby incorporated by reference.

Despite the potential accuracy of x-ray or other photon radiotherapy systems, the ability to control the dose placement is limited by the physics of the photon beam and in particular the fact that the photon beam necessarily irradiates healthy tissue on both sides of an internal tumor as it passes through the patient. Further, the ability to minimize the total irradiation to heathy tissue with multiple beam angles in some cases is severely constrained by the presence of radiation sensitive organs near the tumor. The need to limit radiation to such organs may make some beam angles unavailable, increasing the dose to healthy tissue along the path of the other beam angles.

For this reason, it would be desirable to use protons instead of photons as the source of the radiation. By controlling the energy of the protons, the protons will stop at a precise location within the patient. In this way, tissue on the far side of the tumor with respect to the radiation source (the distal side) receives no radiation dose. Further, because the dose provided by a proton is concentrated at a "Bragg peak" around the area where the photons stop, the dose to healthy tissue on the near side of the tumor with respect to the radiation source (the proximal side) can also be reduced.

In present proton therapy systems, a beam of protons is collimated to the outline of the tumor and adjusted in energy to stop at the far edge of the tumor. Material is then inserted in the proton beam to reduce the energy of the protons and thus draw the point where the protons stop back through the tumor. As the wedge is inserted, the protons deposit an essentially even dose across the tumor. In practice, a rotating wheel with spokes of various thicknesses is inserted in the beam to deposit an even dose across the tumor.

This technique, which continuously exposes the patient to the beam of protons as the spokes are moved through the beam, dramatically increases the dose to healthy tissue on the near side of the tumor, obviating some of the benefits of proton radiotherapy.

SUMMARY OF THE INVENTION

The present invention is an apparatus and therapy method for proton therapy providing more accurate dose placement together with a reduced exposure to tissue outside of a tumor.

The present invention eliminates the need to sweep the Bragg peak of protons through the tumor but rather places the Bragg peak at a fixed location near the distal side of the tumor for each of a variety of different angles. The cumulative effect of the multiple gantry angles provides a uniform dose as opposed to a "sweeping" of the depth of penetration or "range" of the protons at each gantry angle. In this regard, the invention employs a range modulator that allows the Bragg peak of individual rays within the proton beam to be accurately placed at the distal edge of the tumor in a pattern that conforms to the edge of the tumor.

In order that the combined exposure at each gantry angle sum to provide uniform dose to the tumor, when the range of the protons at each gantry angle is fixed and not swept, the intensity of the proton beam at each gantry angle and for a plurality of rays within the proton beam must be independently controlled. Thus, the invention also employs an intensity modulator allowing different rays within the proton beam to have different intensities.

Specifically, the invention provides a method for treating a tumor in a patient, a method used with a proton source that produces a fan beam of protons in a beam plane at a plurality of gantry angles, the beam including a plurality of separate and adjacent rays arranged about one central ray. The method generates a dose map describing the proton dose to be delivered to a patient slice within the beam plane and processes the dose map to produce an intensity sinogram, i.e., a plurality of fluence profiles, each corresponding to different gantry angles in the fan beam plane. Each fluence profile provides independent average fluence values for the protons in different rays of the fan beam as needed to provide a dose of radiation corresponding to the dose map (or being as close as possible to the dose map) when combined with the other fluence profiles of the sinogram. The dose map is also processed to produce a range sinogram including a plurality of range profiles each corresponding to different gantry angles in the fan beam plane. Each range profile provides independent range values indicating the range of travel of the protons for protons in different rays of the fan beam as needed to reach the distal edge of the target. The central ray is rotated with respect to the patient around a single axis perpendicular to the beam plane so that the fan beam radiates the patient slice from the different gantry angles while changing the fluence and range of the protons in each ray according to the intensity and range sinograms.

Thus, it is one object of the invention to provide improved dose placement by constraining the proton exposure to a slice and controlling both the range and intensity of the protons along different rays within a fan beam irradiating the slice.

The rotation of the central ray with respect to the patient may be performed by securing the patient to a rotatable platform and rotating the platform about a single axis. The patient may also be moved upward to provide a helical rotation.

Thus, it is another object of the invention to simplify the construction of an accurate proton therapy system by eliminating the need to bend the path of the protons to different angles about the patient.

The range sinogram may be selected to align a Bragg peak of the protons of each ray of the fan beam with a distal edge of the tumor for each gantry angle.

Thus, it is another object of the invention to reduce "spill-over" dose outside of the tumor by positioning the Bragg peak at the distal side of the tumor so that the sharp fall-off of the distal edge of the Bragg peak defines the dose at the interface between the tumor and healthy tissue. Despite this fixed range of the Bragg peak, control of the intensity of the protons in the various beams for different gantry angles allows a uniform dose to be deposited over the tumorous area without sweeping of the range of the protons at a given gantry angle.

The range that the proton traveled before stopping within the patient depends on the character of the intervening patient tissue. The method may therefore include the step of obtaining a proton verification tomogram of the patient slice and producing the range profiles based on information about the interaction between protons and patient tissue provided by the proton verification tomogram.

Thus, it is another object of the invention to precisely determine the expected range of protons within the patient to obtain highly accurate dose placement.

In accordance with the above object, the invention also provides a method of producing proton tomographic verification images of the patient (as opposed to x-ray tomographic images). The first step of this method requires a generation of protons of a known energy sufficient to permit the protons to pass through the patient without stopping. A beam of protons is directed at the patient from a plurality of angles within a slice plane and along an axis, and the energy of the protons exiting the patient are detected at a plurality of angles and at a series of points displaced by different amounts from the axis. A tomographic verification image is reconstructed of the patient based on the variations in energy detected at the plurality of angles.

Thus, it is another object of the invention to provide a method of assessing the distance protons will travel through the patient so that the proton energy may be precisely tailored to irradiate a given location in the patient.

The detector system may employ a depth sensitive proton detector providing a depth signal, measuring the range of the received protons through a detector medium of predetermined thickness, and a position signal, measuring the location of received protons. A range shifting means positioned between the proton source and the patient independently controls the distance the protons travel along each of the rays so they stop in the detector medium. The detector system further includes a subtracter, subtracting the amount of range shifting provided by the range shifting means to the depth signal provided by the detector to provide energy measurements of the protons in separate rays of the proton beam.

Thus, it is another object of the invention to provide a practical proton range detection system having reduced depth. By pre-scaling the range of the protons, the depth of the detector may be reduced and additional resolution obtained.

The range shifting means used both for radiotherapy and proton tomography may include a plurality of range leaves moving within a rack positioned generally between the radiation source and the patient where the position of each range leaf controls the range of proton travel in a patient along a corresponding ray. An actuator moves the range leaves within the rack. Each range leaf may be a simple wedge shaped block of material so that movement of each range leaf changes the thickness of material through which the protons travel.

Thus, it is another object of the invention to provide a simple and rapid method of independently controlling the range of protons in each ray of the proton beam so that the position where the protons stop may conform to the tumor.

The method of the present invention may be realized for simple dose patterns as a set of blocks having a thickness adjusting the range of the Bragg peak of the protons of the fan beam to a distal edge of a standard area for a given gantry angle, and stopping protons to edges of the standard area that will be distal edges at other gantry angles.

Thus, it is yet another object of the invention to provide a method of implementing the treatment technique of the present invention in simplified form.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Proton Tomotherapy and Tomography Hardware

Figure 1:
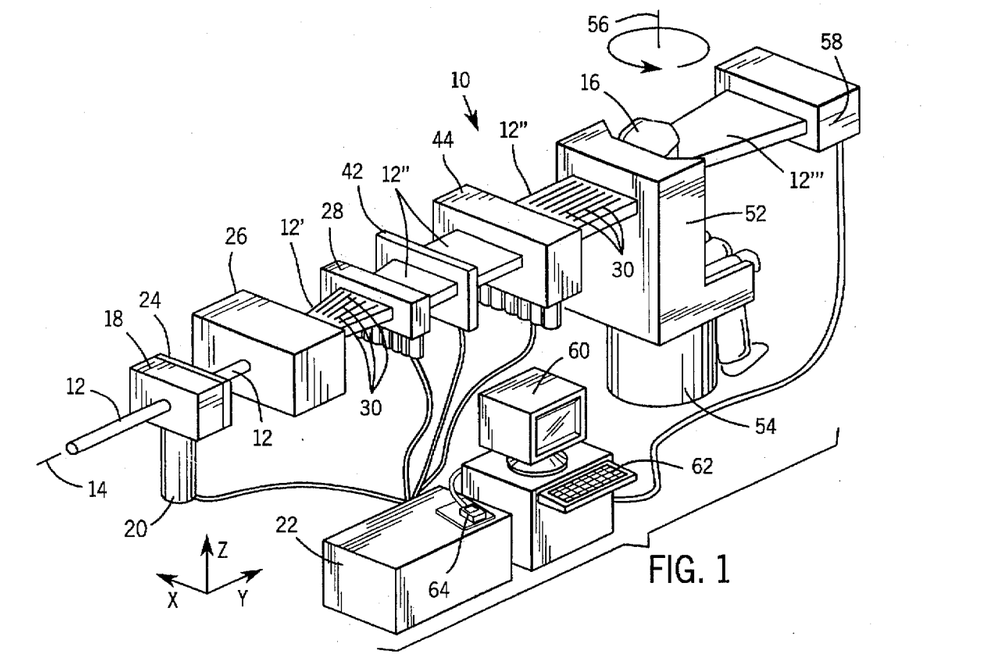
FIG. 1 is a simplified perspective view of a proton tomotherapy system of the present invention in which a stationary fan beam of protons irradiates a patient rotated to different gantry angles on a rotatable chair while each ray of the photon beam is changed in range and intensity by series intensity and range shifting modulators.

Referring to FIG. 1, a proton tomotherapy system 10 for practice of the present invention provides a beam 12 of mono-energetic protons such as may be obtained from a particle accelerator such as a cyclotron or the like.

At present, such proton sources are large and stationary and a set of bending magnets are used to reposition the proton beam to various angles about the patient. Notably, in the present invention such repositioning magnets are not required because the proton beam 12 travels along a stationary axis 14 to the patient 16. Nevertheless, the present invention is also applicable to systems where the proton beam rather that the patient is moved, as may be desired, for example, to reduce organ shifting when the patient moves.

The initial energy of the protons within the beam 12 is determined by the acceleration provided to the protons by a particle accelerator (not shown) according to methods well known in the art. This initial energy may be reduced by a coarse range shifter 18. The term "range shifting" will be used to describe this change in the energy of the proton beam reflecting the fact that a change in energy directly corresponds to a shift in the range of penetration of the protons into the patient.

The coarse range shifter 18 employs a wedge-shaped block (not shown) of a low atomic number material ("low-Z"). The low-Z material provides energy reduction without significant scattering. The wedge-shaped block is driven to different positions within the beam by an actuation motor 20 controlled by a computer 22 whose operation will be described in more detail below. As the wedge is moved into the beam 12, the protons of the beam 12 pass through an increasing thickness of low Z material reducing the energy of all protons correspondingly.

After passing through the coarse range shifter 18, the proton beam 12 crosses a fluence monitor 24 which determines the rate of proton flow (protons per unit time) of the proton beam 12 (henceforth termed "intensity"). The fluence monitor 24 may be a transmission ion chamber-type fluence monitor well known in the art.

It is noted that the intensity or fluence of the proton beam is distinct from the energy of the protons. For example, a proton beam with a single proton with high energy nevertheless has a low fluence whereas a proton beam with many low energy protons has high fluence. As described, the energy of the protons of the proton beam determines the range of penetration of the protons into the patient whereas the fluence or intensity of the radiation beam 12 determines the total dose delivered to the patient.

After range is shifted and intensity monitored, the proton beam 12 then passes to a fan beam former 26 which converts the narrow, cylindrical proton beam 12 into a fan beam 12' comprised of a number of rays 30 of protons diverging from a point within the fan beam former 26 in a generally horizontal plane about axis 14.

The fan beam former 26 may employ a series of scattering foils in conjunction with a slit collimator having a horizontal opening or may make use of the fundamental positive charge of the protons to spread the proton beam 12 into a fan beam 12' with a magnetic field, as is generally understood in the art.

Figure 3:
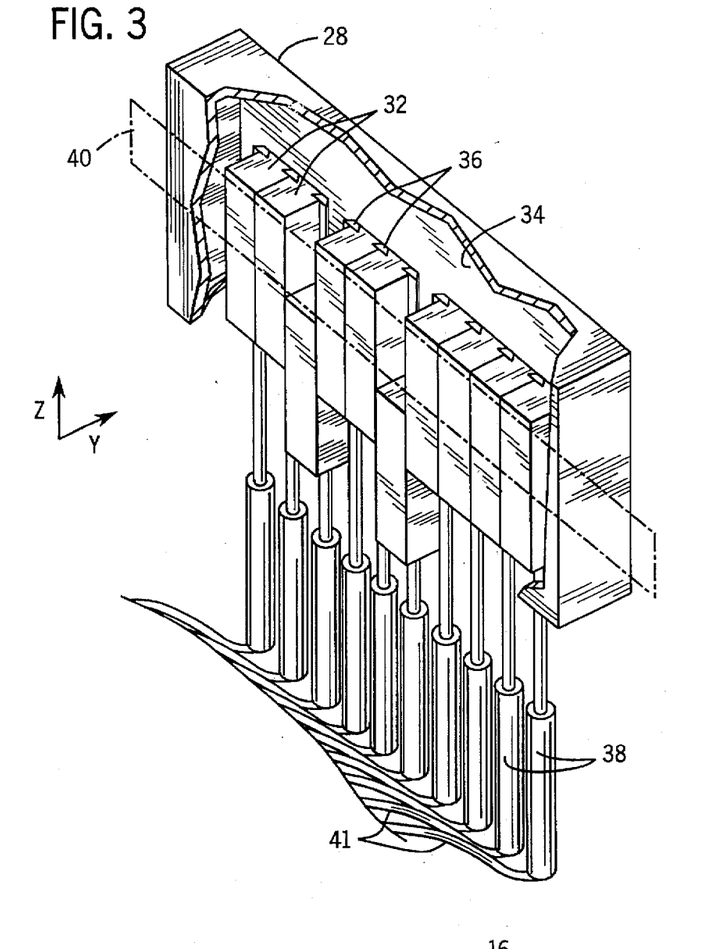
FIG. 3 is a perspective, fragmented view of the intensity modulator of FIG. 1 showing a set of independently movable opaque vanes for controlling the intensity of the protons along the various rays of the fan beam.

The fan beam 12' passes to an intensity modulator 28 which may separately control the intensity of adjacent rays 30 of the fan beam 12'. Referring also to FIG. 3, the intensity modulator provides a plurality of proton opaque vanes 32 abutting each other within an enclosure 34. The vanes 32 may slide upward and downward along guides 36 into and out of a fan beam area 40, the latter representing the cross section of the fan beam 12' in a vertical plane. Guides 36 are constructed of a generally radiolucent material.

The width of each vane in the fan beam area 40 defines the width of each ray 30 of the fan beam 12 whereas the height of each ray 30 of the fan beam 12 is defined by the vertical thickness of the fan beam 12. The number of rays 30 into which the fan beam 12 is divided will affect the accuracy with which the dose may be deposited in the direction perpendicular to the proton axis 14. Generally a larger number of rays 30 provides better resolution in the placement of the dose but increases the complexity of the equipment. In the present embodiment, ten rays 30 are employed and hence ten vanes 32 are required.

When a vane 32 is in position within the fan beam area 40, the intensity of the protons in a ray 30 associated with that vane 32 is reduced to zero. Conversely when a vane 32 is withdrawn from the fan beam area 40, the intensity of the protons in that ray is unattenuated and equal to the intensity of the ray 30 as emitted from the fan beam former 26. Ideally this latter intensity is equal to the intensity of the pencil fan beam 12 divided by the number of rays 30 of the fan beam 12, i.e., the rays of the fan beam 12 are of equal intensity. However, the rays 30 of the fan beam 12 need not be of equal intensity as emitted from the fan beam former 26, because the intensity modulator 28 may provide an effective flattening of the fan beam intensity among rays 30.

The vanes 32 are moved rapidly between an open position outside of the fan beam area 40 and a closed position blocking the fan beam area 40 by one of a set of electromagnetic or pneumatic actuators 38 or other similar actuators well known in the art. The actuation of the pneumatic actuators 38 is controlled by the computer 22 which provides electrical signals to the electromagnetic actuators or to air valves connected via hoses 41 to each pneumatic actuator 38 as will be understood by those of ordinary skill in the art.

Ideally the actuators 38 move the vanes 32 instantaneously between the open and closed positions and the intensity control is provided by changing the ratio of the time the vane 32 is in the open position to the time the vane is in the closed position. This ratio thus defines the average fluence of each ray for an "exposure" of the patient for a given period of time. After each exposure of the patient 16, the patient may be rotated to a new "gantry angle" as will be described below.

It will be recognized to those of ordinary skill in the art that other methods could be used to provide intensity control of a plurality of rays 30 of protons. For example, the flux of protons from the accelerator can be controlled at its source through well known techniques. A pencil beam of controlled flux may be swept magnetically to provide a 'time average' fan beam. Alternatively, wedges of high atomic number material (high-Z) may be used to control the average fluence in individual rays. Protons scattered by the wedges are stopped by collimator plates. Thus, as the wedge is moved into the beam and greater wedge material is intercepted by the beam, increased scatter causes diversion of some protons into the collimator blades decreasing the effective intensity of each beam.

Referring again to FIG. 1, after-the fan beam 12' passes through the intensity modulator 28, it is received by a segmented fluence monitor 42 as an intensity modulated fan beam 12". The segmented fluence detector measures the intensity of each ray 30 to confirm the desired intensity has been obtained. Signals indicating the intensity for each ray 30 are returned to the computer 22 where they are monitored to ensure proper operation of the intensity modulator 28.

Segmented fluence monitor 42 is also used when initially calibrating the tomotherapy system 10. This calibration requires opening all of the vanes 32 within the intensity modulator 28 so that any variation in the fluence distribution of the fan beam 12" among the rays 30 may be detected. Such variations in fluence are used by the computer 22 to modify the signals controlling the intensity modulator 28 and thus to effectively flatten out the fluence of the fan beam 12". This flattening signal is combined with a signal indicating the desired fluence modulation on the fan beam 12 dictated by the desired dose placement in the patient 16. Thus the computer 22 sums a flattening factor and a modulation factor to control the intensity modulator 28.

Figure 2:
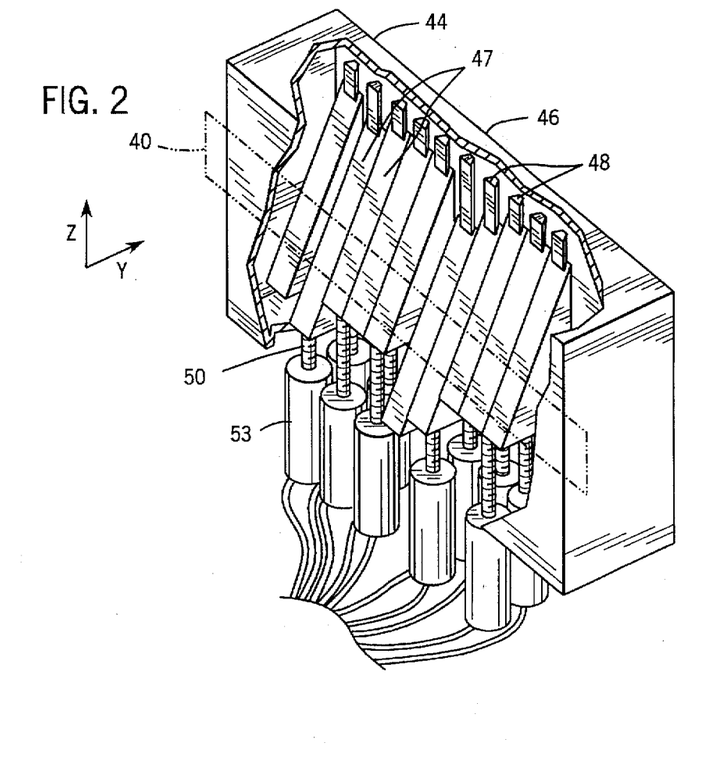
FIG. 2 is a perspective, fragmentary view of the range shifting modulator of FIG. 1 employing a set of movable wedge shaped range shifting elements.

Referring to FIGS. 1 and 2, the protons within the intensity modulated fan beam 12" are then adjusted in range by range modulator 44. Unlike the intensity modulator 28, the range modulator 44 does not significantly decrease the average number of protons per unit time passing along each ray 30, but instead decreases the energy of the individual protons, affecting the distance they penetrate into the patient 16.

The range modulator 44, like the intensity modulator 28, provides a set of vanes 47 moving up and down within an enclosure 46 on tracks 48 so as to move in and out of the fan beam area 40. Each vane 47 is the width of a ray 30 as previously defined by the intensity modulator 28, thus there are ten vanes 47 fitting adjacent to each other. Because of the divergence of the fan beam 12", the vanes 47 will be somewhat wider than the vanes 32.

Nevertheless, vanes 47 are different from vanes 32 in construction and purpose. Whereas vanes 32 stop the protons, vanes 47 are intended only to reduce the energy of the protons and thus their ultimate range. The total mass of the vanes 47 positioned within the fan beam 12" should therefore be comparable to the total mass that the protons will be passing through in the patient 16 and the atomic number of the material of the vanes 47 should be low to minimize the amount of scattering. The vanes 47 may, for example, be graphite or aluminum. The variation in the effective wedge thickness caused by the tracks 48 may be offset by making the vanes 47 thicker on their radiation side at points over the track 48.

In contrast to vanes 32 of the intensity modulator 28 which move rapidly between an open and closed position, the vanes 47 of the range modulator 44 are moved incrementally through the fan beam area 40 by lead screws 50 driven by rotary actuators 53. The vanes 47 are wedge shaped so that as the rotary actuators 53 move the vanes 47 up and down through the fan beam area 40, they interpose additional or less material in the proton path thus causing the protons to stop sooner or later within the patient 16. In this way, a continuously variable adjustment to the range of the protons is obtained.

Signals to the rotary actuators 53 are provided by the computer 22 which also receives feedback from the rotary actuators 53 confirming the location of the vanes 47 as will be generally understood by those of ordinary skill in the art.

It will be understood to those of ordinary skill in the art that the range modulator 44 may be implemented in other ways including using energy modulation of the accelerator and a scanning pencil beam 12.

A fan beam 12''' emerging from the range modulator 44 thus comprises a set of adjacent rays 30 in which the proton intensity and range has been independently controlled, i.e., the intensity and range of each beam is independent from the beams on either side of it. The fan beam 12''' is directed across the patient 16 who is supported by a chair 52, the latter being on a rotating support 54 that may rotate the patient 16 about a rotation axis 56 generally perpendicular to axis 14 and the plane of the fan beam 12'''. The chair 52 may also move upward or downward in a helical pattern.

The movement of the chair 52 permits the fan beam 12''' to expose a slice to the patient 16 at 360° of "gantry angles" determined by the position of the rotating support 54. Additional slices may be exposed by moving the chair 52 up or down. Alternatively, a helical exposure pattern may be obtained by concurrent rotation and vertical movement of the chair 52.

During normal proton therapy, no protons pass through the patient 16, but preferably all are adjusted in range to stop within the tumor, thus eliminating exit dose to healthy tissue. Nevertheless, the above described apparatus may also be used for proton tomography as will be described below. In proton tomography, the range of the protons is adjusted to exit the patient 16. After exiting the patient, the protons of fan beam 12''' are received by a range detector 58 which can evaluate the range of the protons in each ray 30 as pass through the patient 16. Proton range and position signals from the range detector 58 are provided to the computer 22. By the convention of this application, the range signals so provided are with reference to a plane of the range detector 58 furthest from the radiation source and positive in the direction from that plane toward the radiation source. Thus, greater range reduction by tissue of the patient causes a more positive range signal.

Computer 22 is a general purpose computer as is well known and used in the field of computed tomography and may include an array processor necessary for calculation intensive image reconstruction. Computer 22, as is normal practice in the art, is connected to a display 60 being a standard monitor as well as a keyboard 62 and cursor control device 64 (such as a mouse or track-ball) both which may be used to enter operator commands and to describe the desired dose on slice images of the patient 16 as will be described further below.

Treatment of a Tumor Slice

Figure 4:
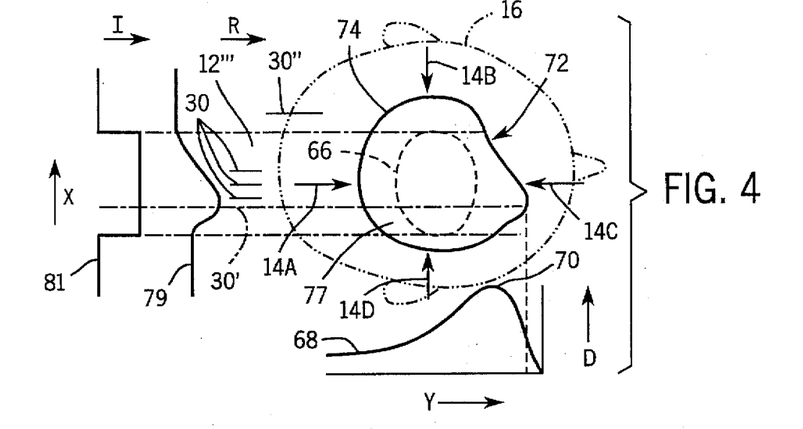
FIG. 4 is a diagrammatic view of a tumor in cross-section showing a plotted intensity and range of the rays of the proton beam controlled per the present invention at one gantry angle and showing the dose generated by protons along one ray within that proton beam.

Referring now to FIGS. 1 and 4, a slice through tumor 66 within the patient 16 can be treated by the proton fan beam 12'''. During treatment, the fan beam axis 14 is positioned at a variety of discrete angles about the patient 16 by virtue of rotation of the patient 16 on chair 52 described above. In FIG. 4, four gantry angles are shown indicated by axes 14(a)-(d), however in actual practice, on the order of ten to one hundred discrete gantry angles may be used for the treatment of the slice of the tumor 66. After each slice is treated, the height of the patient is indexed and another slice may be treated.

At each gantry angle, the intensity of each ray 30 of the fan beam 12''' (forming an intensity profile) and the range of the protons in each ray 30 of the fan beam 12''' (forming a range profile) are set to a predetermined value determined by the computer 22 during a treatment planning process and held constant for that gantry angle. The determination of the necessary range and intensity profiles will now be described.

For each ray 30 of the fan beam 12''', the protons provide a dose to tissue along their path as shown by dose deposition curve 68. Specifically, the dose deposition curve 68 indicates the dose deposited by one ray 30' of the fan beam 12''' as it passes through the patient 16 as a function of distance y through the patient along the proton axis 14. As shown, the dose received by the patient generally increases as the depth of the proton increases and the proton slows. At Bragg peak 70, the dose increases to a maximum value as most protons stop. The dose drops off rapidly after the Bragg peak and reaches nearly zero indicating a complete stoppage of all protons. Thus, the Bragg peak is a statistical phenomenon—for mono-energetic protons, the exact stopping distance will vary with most protons stopping at the Bragg peak; nevertheless, this dose deposition curve 68 for large numbers of protons is well defined.

The present inventors have determined that a preferred method of adjusting the range and intensity of the fan beam 12''' for different gantry angles about the patient 16 and tumor 66 is to adjust the range of the protons of each ray 30 so that the Bragg peak 70 is positioned substantially at a distal edge 72 of the tumor 66. The distal edge 72 is as before that edge furthest from the source of the protons and thus will change with changing gantry angles.

Accordingly, the range of the protons in each proton ray 30 are adjusted on a beam by beam basis to match the distance the protons in that ray 30 have to travel to stop substantially at the distal edge of the tumor 66. The range profile 79 across the fan beam 12''' mirrors the outline of the distal edge 72 of the tumor 66.

Employing this range setting, the sharp fall-off of the dose deposition curve 68 (on the side of the Bragg peak 70 away from the radiation source) is positioned at the boundary between the tumor 66 and surrounding healthy tissue whereas the gradual fall-off of the dose deposition curve 68 (on the side of the Bragg peak 70 toward the radiation source) is positioned within the tumor 66.

Using this strategy, one gantry angle produces considerably more dose on the distal edge 72 of the tumor 66 than in its center or proximal side. This uneven dose distribution is remedied not by sweeping the range of the protons through the tumor 66 but by means of the cumulative effect of dose at different gantry angles employing the same strategy. Thus, at a gantry angle in which the proton axis 14 is at position 14(c), the edge 72 (now of the proximal edge) will receive far less dose, whereas the previous proximal edge 77 (now the distal edge) will receive a comparatively greater dose.

The difference in height between the Bragg peak 70 and the dose deposition curve 68 at the proximal edge 77 is generally a fixed function of the patient material and this fact would seem to provide a natural limit to how many pantry angles may be employed if a uniform dose within the tumor 66 is to be obtained. To the contrary however, the ability to control both the range and fluence of the rays 30 of the fan beam 12''' allow this technique of placing the Bragg peak at the distal edge to be used for an arbitrary number of gantry angles. For example, the intensity of rays 30'' that would normally expose a region 74 of the tumor 66 that will be a distal area for a later gantry angle (14(d)) can be intensity modulated by intensity profile 81 to be zero at gantry position 14(a) thus preventing over accumulation of dose.

Thus, the asymmetry of the dose deposition curve 68 may be used advantageously to provide a sharp demarcation in dose between healthy and tumorous tissue while at the same time providing a uniform dose across the tumor 66 built up by using a variety of gantry angles.

Proton Tomotherapy for Standard Zones

Figure 5:
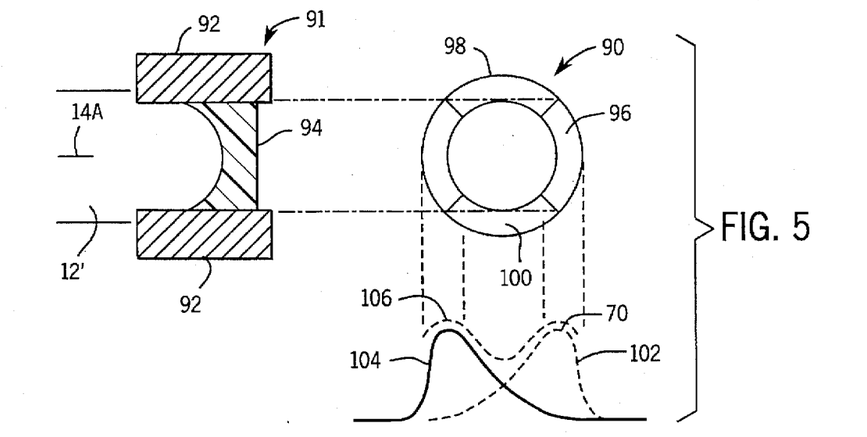
FIG. 5 is a diagrammatic view of a standard circular cross-sectional treatment zone such as may be irradiated using the method of the present invention with a specially designed attenuating block and showing the dose produced by that block together with the cumulative dose produced by two angles of the radiation.

Referring now to FIGS. 4 and 5, the technique of placing the Bragg peak 70 at the distal edge of the tumor can be used to develop a set of blocks 91 for treating predetermined zones 90 within the patient without the need for intensity modulators 28 or range modulators 44 as have been previously described. An example block 91 imposed in front of the fan beam 12' includes two flanking intensity control portions 92 which serve to collimate the fan beam 12' to a width less than the projected width of the area 90 along the fan beam axis 14. In between these flanking blocks 91 is a range control portion 94 of low-Z material providing an adjustment to the range of the protons of the fan beam 12' so that their Bragg peaks 70 are positioned at the distal edge 96 of the area 90.

For the case of a circular area 90, the range control portion 94 is narrower at the center of the fan beam 12' to provide the greatest range for center protons and greatest at the edges so as to decrease the range of those protons so they conform to the distal edge of the circular area 90. As described before, the block 91 serves to shield areas 98 and 100 which will be distal areas for other fan beam angles.

At the first gantry angle indicated by axis 14(a), total dose provided by block 91 is indicated by curve 102 showing the Bragg peak 70 position near the distal edge 96. At a second gantry angle, 180° removed from axis 14(a), a second dose indicated by curve 104 is deposited providing accumulative dose 106 having sharp edges at the edges of zone 90 but a somewhat reduced dose in the center of zone 90. Additional gantry angles removed from axis 14(a) by plus 90° and minus 90°, respectively, serve to fill in the center area of zone 90. Thus with a simple block 91 and multiple gantry angles, near uniform deposition of dose in a predefined regular zone 90 can be obtained with rapid fall off of the dose Outside of the zone 90 provided the Bragg peak 70 is placed near the distal edge in each gantry angle.

It will be understood from the above discussion that multiple blocks could be used to provide a standard zone that is not circular. It will be understood that the portions 92 and 94 may be overlapping and that portions 92 may provide simple attenuation as well as the complete blocking of protons shown.

General Proton Tomotherapy

Figure 7:
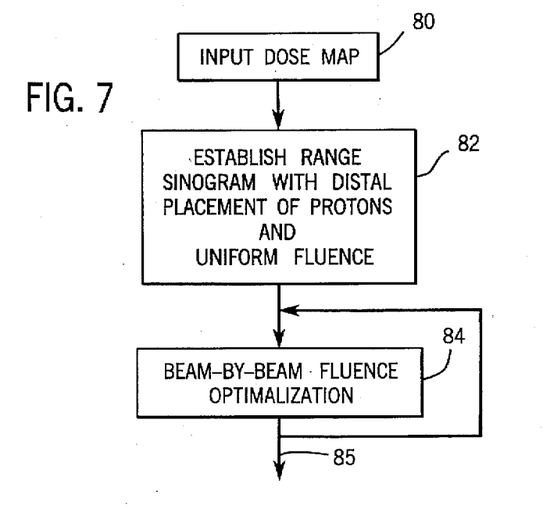
FIG. 7 is a flow chart showing the steps of one method of generating the necessary ranges and fluences for practice of the present invention.

Referring now to FIGS. 1, 4 and 7, generally more complex intensity and range profiles 81 and 79 will be used exploiting the capability of the intensity modulator 28 and the range modulator 44. The procedure for determining the intensity profiles and range profiles of the fan beam 12''' at the variety of gantry angles first requires that a dose map be established as indicated by process block 80. This dose map describes those areas of a slice of the patient 16 to be treated that require a dose (specified as a minimum dose) and if applicable, those areas which cannot accept too much radiation (defined as a maximum dose) such as radiation sensitive organs. The dose map may be established by projecting a tomographic image of the slice of the patient 16 on the display screen 60 and allowing the physician or radiologist to trace areas to be treated or to be excluded from treatment with the cursor control device 64. These regions are assigned numerical dose limits.

At process block 82, the dose map is evaluated by computer 22 at each of the different gantry angles, the number of which may be selected by the radiologist depending on the accuracy of the treatment required and the time permitted. At each gantry angle, an intensity profile 81 (such as shown in FIG. 4) indicating the intensity of each ray 30 of the fan beam 12''' and a range profile 79 (such as shown in FIG. 4) indicating the range of each proton of each ray 30 in the fan beam 12''' is established.

In one embodiment, the intensity profile 81 is initially set to be zero by the computer 22 for all rays 30'' that do not intersect the tumor 66 or that intersect a zone in which radiation should be excluded (not shown). The value for rays 30 intersecting the tumor 66 are set to a value equal to the total dose desired in the tumor 66 divided by the number of gantry angles. As will be understood, this initial setting need not be precise at this point but will be corrected by an iteration described below.

The range profiles 79 for each gantry angle are set as has been previously described so that the Bragg peaks 70 of protons in the rays 30 are positioned at the distal edges 72 of the tumor for each gantry angle.

At process block 84, the initial intensity profiles 81 and range profiles 79 are used by the computer 22 to calculate an actual dose that would be received over the slice being treated. In one embodiment, patient tissue is assumed to be uniform and equivalent to that of an equal volume of water in calculating the range of the protons within the patient 16. Normally this dose computed above with the initial intensity profiles 81 and range profiles 79 will deviate from the desired dose entered by the physician at block 80.

Accordingly, also at block 84, the intensity profiles 81 and range profiles 79 are optimized in the following procedure. For each intensity profile 81, the intensity of each ray 30 of each fan beam 12 for each gantry angle is adjusted incrementally by the computer 22 upward and then downward and the dose recomputed. This recomputed dose is compared to the previous dose to see if it conforms more closely to the desired dose. Additional increments in that beam are made until no further improvement is obtained. This process is then repeated for the next beam of that intensity profile for that gantry angle.

Once each of the beams of a given intensity profile have been optimized in this manner, the same procedure is applied to the next gantry angle until all intensity profiles have been optimized.

At the conclusion of this process indicated by arrow 85, an optimized set of intensity and range profiles 81 and 79 for each of the gantry angles are obtained. These profiles 81 and 79 are used in the control of the proton tomotherapy machine by the computer 22 during actual treatment of the patient 16 as the patient 16 is rotated about axis 56.

General Proton Tomography

Figure 6:
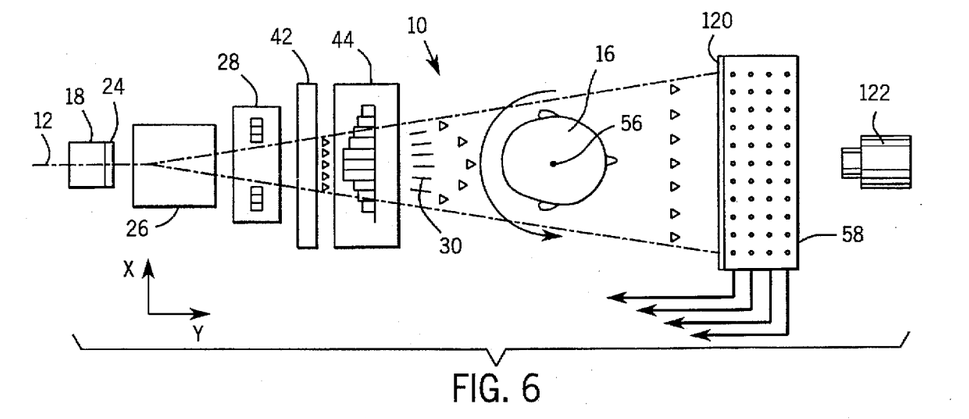
FIG. 6 is a plan view of the system of FIG. 1 in schematic form showing the generation of a proton beam for proton tomography such as may be used with the present invention.

Referring now to FIGS. 6 and 7, it will be understood that the precision by which the range of the protons can be controlled during proton tomotherapy is dependent on how much is known about the patient tissue through which the protons will travel in reaching the tumor 66. Thus, it is desirable both from the point of view of generating the initial dose map of process block 80 and from the point of view of determining the precise range of the protons of each ray 30 in calculating dose in process block 84, that a tomographic verification image of the patient at the treatment area be obtained such as indicates the effect on patient tissue in stopping protons.

Normal x-ray tomography is imperfect for this purpose. Although it may be used to accurately identify the outlines of the tumor 66, x-ray attenuation as measured by an x-ray tomogram is a function of both the atomic number and the electron density. In contrast, the range of protons is dependent primarily on electron density alone and cannot be easily predicted from a single energy x-ray tomogram.

For this reason, it will be preferable to obtain a tomographic verification image measured with protons rather than x-rays and based on proton range effects rather than changes in fluence. Ideally such tomogram is obtained on the same equipment used for the proton tomotherapy thus eliminating equipment variations and patient alignment problems.

Referring to FIG. 6, the proton tomography system 10 employs the same elements previously described for the proton tomotherapy system of FIG. 1, that is a proton beam 12 receives a coarse range adjustment by coarse range shifter 18 and is turned into a fan beam 12'' by fan beam former 26. For proton tomography, the intensity modulator 28 is fully opened with its vanes 32 outside of the fan beam area 40 to provide a fan beam 12''' sufficient to completely subtend the patient 16 at each of the gantry angles required by the tomography algorithms. The width of the beam is verified by fluence monitor 42.

The range modulator 44 is used to pre-adjust the range of the protons of rays 30 generally increasing the range of the center rays 30 so that after they pass through the patient 16, the protons will reach but not pass completely through the detector 58. In particular, it is desired that the protons stop within the medium of detector 58 so that their exact range may be determined. For this purpose, the coarse range shifter 18 is also used to increase the range of the protons.

As the protons enter the range detector 58, they are slowed within a detector medium, such as a gas contained in that detector 58, causing an ionization which is detected by a series of crossed wires at different depths. By appropriate segmentation of the detector to form individual parallel plate ion chambers, an appropriate determination of the proton range is accomplished. By using two planes of wire ionization chambers, the range and proton trajectory are determined.

Thus, the detector 58 provides indication as to the location in x and z of the protons passing through the patient and the protons range (y) according to the depth of the wire receiving the charge.

In addition, an initial level of scintillating material 120 may be placed on the detector 58 and monitored with a camera 122 to provide location information.

The range shifting caused by the range modulator 44 and the coarse range shifter 18 is subtracted from the depth signals provided by the detector 58 to isolate the range shifting effect of the patient tissue.

It will be understood that an extremely small number of photons may be used for this imaging process which measures not fluence but range.

The range information provided by the protons passing through the patient, comprising a set of range numbers linked to spatial coordinates across the fan beam, are collected for a series of gantry angles, typically over 360°, and reconstructed according to conventional computed tomography techniques to provide a tomographic verification image of the patient. Because proton range rather than x-ray fluence is used, however, the contrast between tissues in the resultant tomographic verification image reflect the varying effect of the tissues on the range of protons passing through those tissues. This information may be used in process block 82 to more accurately adjust the range modulator 44 to place the Bragg peak 70 of the protons at the distal edge of the tumor 66.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

We claim:

1. In a proton therapy machine having a proton source for producing a proton beam directed toward a patient at a gantry angle, the beam including a plurality of adjacent rays dispersed within a beam plane, a modulator comprising:

an intensity control means for independently controlling the fluence of the protons along each of the rays; and a range shifting means for independently controlling the distance the protons travel through the patient along each of the rays.

2. The modulator as recited in claim 1 wherein the intensity control means includes:

a plurality of fluence leaves moving within a rack positioned generally between the radiation source and the patient and guiding the fluence leaves between a closed state within the proton beam where each fluence leaf blocks the protons along one ray, and an open state where each fluence leaf permits passage of protons along one ray;

an actuator moving the fluence leaves between the open and closed state; and a timer communication with the actuator to control the ratio of the period of time during which each fluence leaf is in the closed state to the period during which each fluence leaf is in the open state to control the average energy fluence of the protons along each ray.

3. The modulator as recited in claim 1 wherein the intensity control means includes:

a plurality of fluence leaves moving within a rack positioned generally between the radiation source and the patient where the position of each leaf controls the scattering of protons traveling along a corresponding ray;

an actuator moving the leaves within the rack; and a collimator for blocking from the patient the protons scattered by the fluence leaves.

4. The modulator as recited in claim 1 wherein the range shifting means includes:

a plurality of range leaves moving within a rack positioned generally between the radiation source and the patient where the position of each range leaf controls the range of proton travel in the patient along a corresponding ray; and an actuator moving the range leaves within the rack.

5. The modulator as recited in claim 4 wherein the range leaves are wedge shaped blocks of material so that movements of each range leaf changes the thickness of the material through which protons travel.

* * * * *